United States Patent [19]

Kensey

[11] Patent Number: 4,852,568

[45] Date of Patent: * Aug. 1, 1989

[54] METHOD AND APPARATUS FOR SEALING AN OPENING IN TISSUE OF A LIVING BEING

[75] Inventor: Kenneth Kensey, Hinsdale, Ill.

[73] Assignee: Kensey Nash Corporation, Exton, Pa.

[*] Notice: The portion of the term of this patent subsequent to May 17, 2005 has been disclaimed.

[21] Appl. No.: 138,245

[22] Filed: Dec. 28, 1987

Related U.S. Application Data

[63] Continuation of Ser. No. 15,267, Feb. 17, 1987, Pat. No. 4,744,364.

[51] Int. Cl.⁴ ............................................. A61B 17/04
[52] U.S. Cl. ................................ 128/325; 128/334 R; 128/897; 623/1
[58] Field of Search ............... 604/15, 60, 285, 288; 128/325, 334 R, 334 C, 335, 207.15, 924 R, 155, 831, 843, 865, 887, 897, 898, 899; 623/1, 11, 12; 128/924 R, 155, 831, 843, 865, 887, 897, 898, 899; 600/32

[56] References Cited

U.S. PATENT DOCUMENTS

| | | | |
|---|---|---|---|
| 3,447,533 | 6/1969 | Spicer | 600/32 |
| 3,516,403 | 6/1970 | Cournut | 604/158 |
| 3,540,431 | 11/1970 | Mobin-Uddin | 128/325 |
| 3,675,639 | 7/1972 | Cimber | 604/60 |
| 3,874,388 | 4/1975 | King et al. | 128/334 C |
| 4,007,743 | 2/1977 | Blake | 128/334 C |
| 4,154,226 | 5/1979 | Hennig et al. | 600/32 |
| 4,577,631 | 3/1986 | Kreamer | 128/303 R |
| 4,710,192 | 12/1987 | Liotta et al. | 128/325 |
| 4,744,364 | 5/1988 | Kensey | 128/334 R |

FOREIGN PATENT DOCUMENTS

0782814 11/1980 U.S.S.R. ............................ 128/334 R

Primary Examiner—Stephen C. Pellegrino
Assistant Examiner—Ralph Lewis
Attorney, Agent, or Firm—Caesar, Rivise, Bernstein, Cohen & Pokotilow, Ltd.

[57] ABSTRACT

A device for sealing an opening or puncture in the wall of a blood vessel, duct or other lumen of a living being. The device includes an elongated tubular body having an outlet at the distal end thereof and which is arranged to be inserted, such as percutaneously, through the puncture in the blood vessel so that the outlet is located within the vessel's interior. An expandible closure is disposed within the tubular body and is formed so as to be held in a compact configuration therein. The tubular body also includes ejecting means for forcing the closure out of the outlet into the interior of the blood vessel, whereupon the closure automatically expands to form an enlarged engagement surface. A retraction filament is secured to the closure for pulling it to the puncture after the tubular body has been withdrawn from the puncture so that the engagement surface of the closure means hemostatically engages the inner surface of the blood vessel contiguous with the puncture. The filament held taut and taped or otherwise secured in place on the patient's skin to hold the closure in position. The closure and filament are each formed of a biodegradable material to enable the closure to be left in place. Preferably the closure also includes a non-thrombogenic coating on its surface. The closure is constructed so that when it is opened and is in place sealing the puncture in the blood vessel it doesn't appreciably block the flow of any blood through the blood vessel.

19 Claims, 2 Drawing Sheets

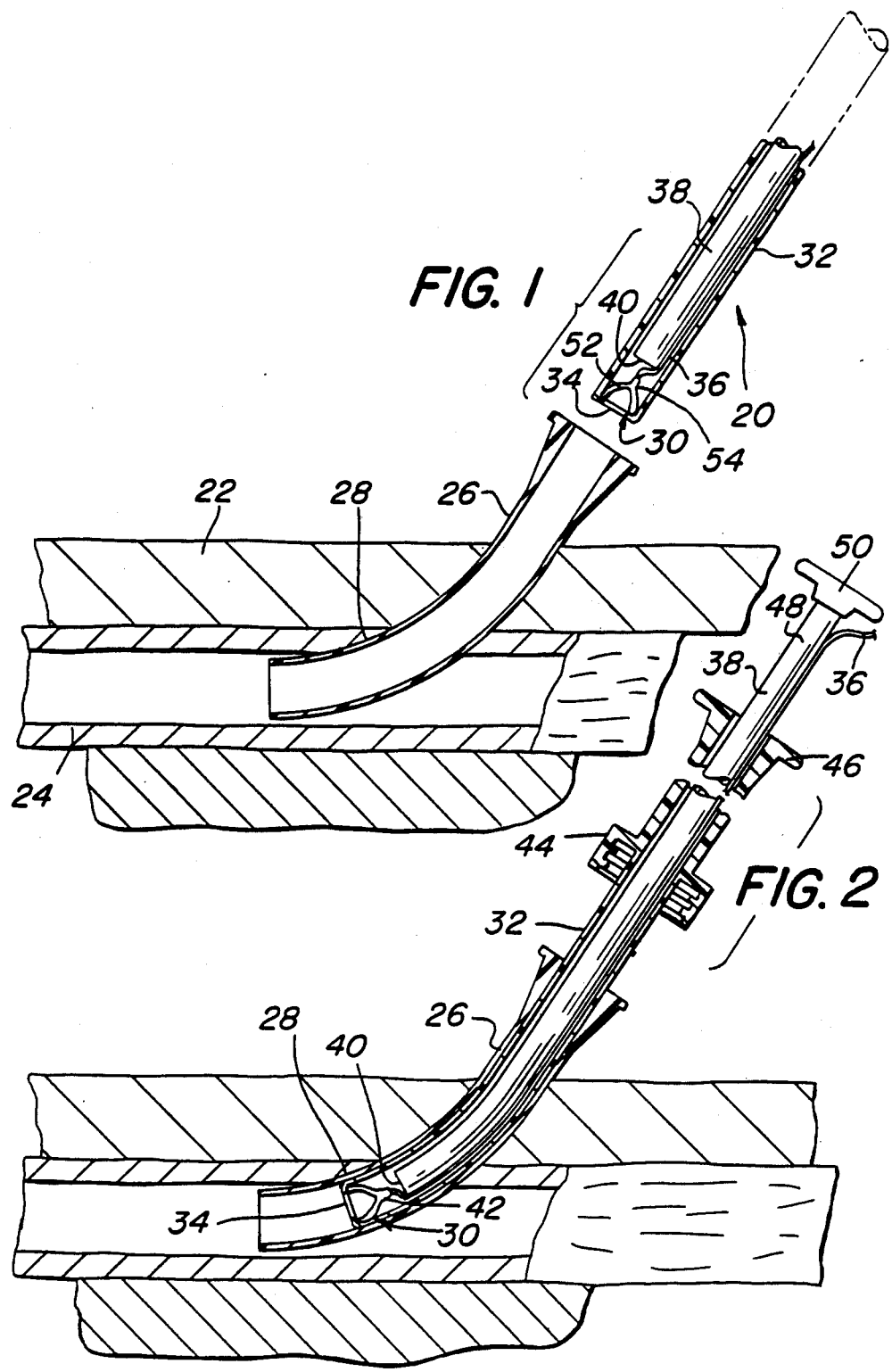

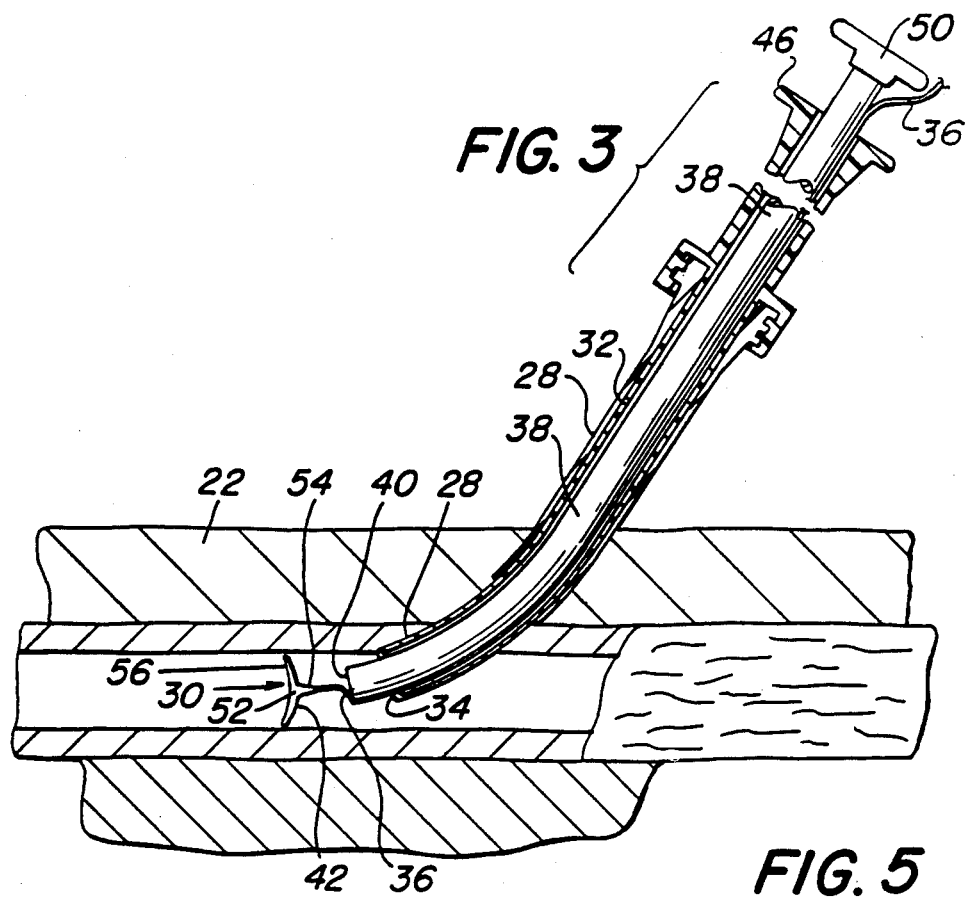
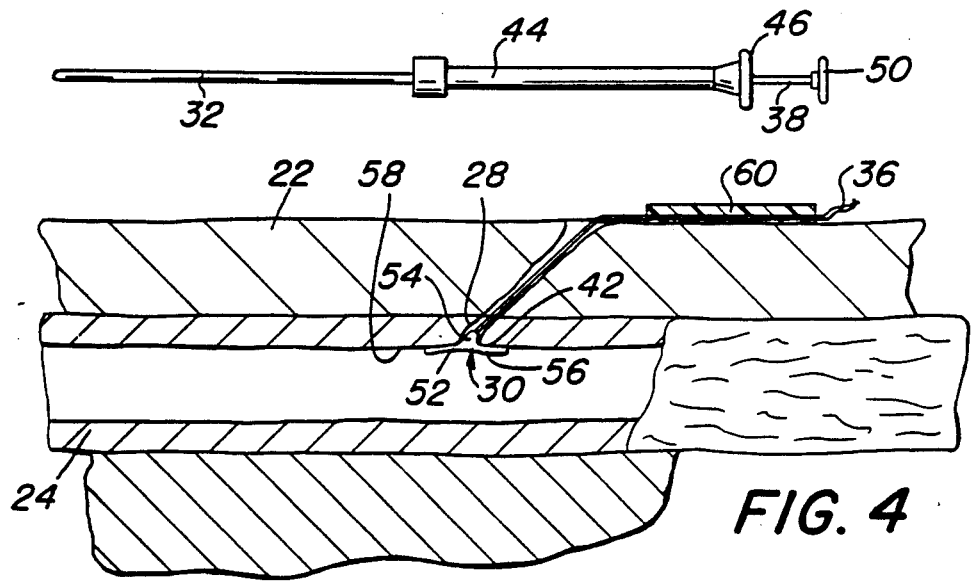

METHOD AND APPARATUS FOR SEALING AN OPENING IN TISSUE OF A LIVING BEING

RELATED APPLICATION

This application is a continuation application of co-pending U.S. patent application Ser. No. 07/015,267, filed on Feb. 17, 1987, and entitled "Device for Sealing Percutaneous Puncture in a Vessel."

BACKGROUND OF THE INVENTION

This invention relates generally to medical devices and more particularly to hemostatic devices.

As will be appreciated by those skilled in the art various surgical procedures are now being carried out intravascularly or intralumenally. For example in the treatment of vascular disease, such as atherosclerosis, it is a common practice to invade the artery to insert an instrument, e.g., a balloon or other type of catheter to carry out the procedure within the artery. Such procedures usually involve the percutaneous puncture of the artery so that an introducer sheath can be inserted into the artery and thereafter the instrument, e.g., catheter, itself can be inserted through the sheath to the operative position within the artery. Such procedures unavoidably present the problem of stopping the bleeding at the percutaneous puncture after the procedure has been completed and after the instrument (and any introducer sheaths used therewith) have been removed. At present such bleeding is stopped by the application of direct digital pressure over the puncture site by a trained physician or other suitably trained medical personnel. Such direct pressure has to be applied for a sufficiently long time for hemostasis to occur so that the opening is effectively closed against further bleeding. In the case of punctures into femoral or superficial femoral arteries the pressure may have to be applied for as long as forty-five minutes for hemostasis to occur. Not only is this direct digital pressure application procedure wasteful of time by highly skilled medical professionals, the procedure results in a substantial reduction, if not virtual arrest, of the flow of blood through the vessel. Since thrombosis is one of the major calamities that can occur in the immediate post operative period, any reduction in blood flow, such as caused by the application of digital pressure, is undersirable.

Applicator devices have been disclosed in the patent literature for inserting an absorbent plug or member into the vagina. Such devices basically comprises a tubular element adapted to be inserted into the vagina and having a plug of absorbent material located therein. The device also includes a plunger to push the plug out of the tubular element into the vagina. The plug also includes a thread or string attached to it to enable the plug to be retrieved from the vagina. Examples of such devices are shown in U.S. Pat. Nos. 1,191,736 (Roberson) and 1,794,221 (Washburn et al.).

While such devices are suitable for their intended purposes, there is no suggestion of their use, nor are they suitable for insertion into an opening in the wall of a blood vessel or other bodily lumen or duct to seal that opening.

The patent literature also includes devices for closing an opening in a blood vessel using sutures, see U.S. Pat. No. 4,587,969 (Gillis). Other means and techniques for closing a wound are disclosed in U.S. Pat. No. 4,606,337 (Zimmermann et al.).

None of the prior art teaches the use of simple means for effecting the closure of an opening, e.g., puncture, in the wall of a blood vessel, duct or lumen, by plugging the opening and without requiring sutures or the application of digital pressure.

OBJECTS OF THE INVENTION

Accordingly, it is a general object of the instant invention to provide a device which overcomes the disadvantages of the prior art.

It is a further object of the device that is effective for closing off a puncture or other opening in a blood vessel, duct or lumen without the need for the application of digital pressure thereto and without resulting in any substantial reduction of blood flow through the vessel.

It is still a further object of the instant invention to provide an instrument which is simple in construction and can be readily inserted into a blood vessel, duct or lumen to position a closure therein for hemostatically sealing the puncture and without substantially blocking the flow of fluid through the vessel, duct or lumen.

SUMMARY OF THE INVENTION

These and other objects of the instant invention are achieved by providing a device for sealing an opening in the wall of a blood vessel, duct or lumen of a living being. The device comprises a tubular body having an outlet at the distal end thereof and which is adapted to be inserted through the opening in the blood vessel, duct or lumen so that the outlet is located within the vessel, duct or lumen. The device also includes an expandable closure disposed within the tubular body and formed of a material to enable it to be held in a compact configuration with the tubular body. The device further includes ejecting means to push the closure out of the outlet into the interior of the vessel, duct or lumen, whereupon the closure expands to form an enlarged wall engagement surface. The device also includes retraction means to move the closure into the opening in the vessel, duct or lumen after the tubular body has been withdrawn from the opening so that the wall engagement surface of the closure hemostatically engages the inner wall of the vessel, duct or lumen contiguous with the opening, thereby sealing the opening. The retraction means also serves to hold the closure in place. The closure is shaped so that when it is opened and in place on the inner wall of the vessel, duct or lumen it does not appreciably block the flow of any fluid therethrough.

BRIEF DESCRIPTION OF THE DRAWING

FIG. 1 is a side elevational view partially in section showing a portion of a device constructed in accordance with this invention about to be inserted into a conventional sheath extending through a percutaneous puncture into an artery;

FIG. 2 is a side elevational view of the device 20 in place in the sheath;

FIG. 3 is a side elevational view of the device 20 during the expulsion of its puncture sealing closure into the artery;

FIG. 4 is a side elevational view of the artery showing the sealing closure in place to close off the percutaneous puncture; and FIG. 5 is a reduced plan view of the device 20 of the subject invention.

DESCRIPTION OF THE PREFERRED EMBODIMENT OF THE INVENTION

Referring now in greater detail to the various figures of the drawing wherein like reference characters refer to like parts, there is shown generally at 20 in FIG. 1 an instrument for effecting the closure of a puncture or other opening in a blood vessel, duct or lumen in a living being. The device 20 thus has particular utility when used in connection with intravascular procedures, such as angiographic dye injection, balloon angioplasty and other types of recanalization of atherosclerotic arteries, in-situ valvulectomy, etc. However, it should be appreciated that the device 20 can be used to hemostatically close a puncture or other opening in other types of duct or lumens within the body. Thus, it is to be understood that while the description of the invention as contained herein is directed to closing off percutaneous punctures in arteries, the device 20 has much more wide-spread applications.

Before describing the instrument 20 itself a brief description of a typical, conventional, intravascular surgical procedure, e.g., catheter instrumentation of an artery, utilizing a percutaneous incision or puncture will be given to best appreciate the features of the device 20. In such a procedure a cannula of an instrument, such as an angiographic needle (not shown), is inserted percutaneously through the skin into the artery, such as the femoral artery 24 at the situs for the instrument's insertion. The needle cannula is held in place and the flexible end of a mini-guidewire (not shown) is then passed through the cannula into the artery to the desired depth (i.e., longitudinal position therealong). Once the mini-guidewire is in place the needle cannula is removed leaving the guidewire in place. A conventional introducer sheath 26 and an arterial dilator (not shown) are then passed over the guidewire through the puncture 28 and into the artery 24. The guidewire and then the dilator are removed leaving the sheath 26 in place. The catheter (not shown) or other intravascular instrument (not shown) is then inserted through the introducer sheath 24 and threaded down the artery to the desired intravascular location, e.g., the situs of an atherosclerotic occlusion. Once the intravascular procedure (e.g., angioplasty) has been completed the catheter is removed. Thereafter the sheath is removed and the surgeon or other trained person applies digital pressure to the percutaneous puncture until hemostasis has occurred.

The device 20 effects the hemostatic closure of a percutaneous or other type of puncture, incision or opening in an artery or other body duct or lumen without necessitating the application of pressure thereto. Thus, once the catheter or other intravascular instrument has been removed but with the sheath 26 left in place, the device 20 of the subject invention is inserted through the sheath 26 into the artery 24 and operated to expel a closure member 30 (to be described later) into the artery. The closure is arranged to be drawn back into the puncture 28 to seal it. The sheath is removed and the closure left in place. Due to its construction the closure is ultimately absorbed by the surrounding tissue.

As can be seen in FIG. 1 the device 20 basically comprises a tubular body 32 having an outlet 34 at its distal end, the heretofore identified closure member 30 having a retraction filament 36 connected thereto, and pusher means 38. The tubular body is an elongate member preferably constructed of a sufficiently small outside diameter, e.g., 8 F (French), and somewhat flexible material, such as polyethylene or polyvinylchloride, to enable it to be inserted through the introducer sheath 26 into the artery 24, with the tubular body's outlet 34 within the artery distally of the puncture 28.

The closure member 30 is an expandable member which, when contracted or compressed is sufficiently compact to fit within the interior of the tubular body 32, but when unconstrained by the tubular body it expands to an enlarged configuration (See FIGS. 3 and 4) suitable for closing off the puncture 28 in the artery. Thus, closure member 30 is formed of a resilient, hemostatic material, which is preferably biodegradable, so that it need not be removed after placement. One particular effective material is a porous hemostatic absorbable gelatin sold by Johnson & Johnson, Inc. under the name Gelfoam.

The pusher means 38 basically comprises an elongated, cylindrical rod-like member, having a distal end 40. The pusher is also formed of a relatively flexible material, such as polyethylene or polyvinylchloride and is disposed within the interior of tubular body 32. The outside diameter of the pusher is slightly less than the inside diameter of the tubular body portion to enable the pusher to be manually moved (slid) down the longitudinal axis of the body portion 28, to push or force the closure 30 out of the outlet 34. Thus the pusher is arranged to be moved from a retracted position, like that shown in FIG. 2 to an extended position like that shown in FIG. 3 wherein its distal end 40 is located close to the outlet 34 of the body 32. When the pusher is moved to the extended position its distal end forces the closure member 30 out of the outlet 34.

The heretofore identified retraction filament 36 constitutes an elongated thread, preferably formed of a long, yet very thin, biodegradable material, such as an absorbable suture, and is fixedly secured to the proximal side 42 of the closure member 30 at the middle thereof. When the closure is in position within the tubular body the thread 36 extends down the length of the tubular body 32 between it and the pusher 38 so that the proximal end of the thread is located outside the device 20.

The thread 36 being long and thin does not interfere with the operation of the pusher expelling the closure member 32 out of outlet 34. Thus, during the expulsion of the closure into the artery the thread 36 slides down the tubular member with the closure. The thread 36 is sufficiently long that a substantial length extends outside of the proximal end of the device 20 even after the closure is in the artery.

In order to effecuate the movement of the pusher from the retracted to the extended position the tubular body includes a collar 44 having a flanged projection 46 arranged to be grasped by the fingers of the user of the device 20. In addition the proximal end 48 of the pusher 38 includes an enlarged cap 50 arranged to be engaged by the user's thumb. Thus, to effect the ejection of the closure member 30 all the user of the device 20 merely has to do is to grasp the projection 46 with his/her fingers while applying pressure to the cap 50 with his/her thumb. This action forces the pusher down the tubular body to the extended position.

As can be seen in FIGS. 3 and 4, when the closure member 30 is in its unconstrained state (such as when it is ejected into the artery) it assumes a configuration having an enlarged head portion 52 and an anchor portion 54. The head portion is of generally disk-like shape of relatively large diameter, e.g., 6–9 mm, yet relatively thin, e.g., 1–2 mm. The head portion includes the rear (proximal) surface 42 and a front (distal) surface 56. The anchor portion 54 consists of a small diameter, e.g., 2–3 mm, hub-like projection from the proximal surface 50 at approximately the center thereof. The distal end of the retraction thread 36 is fixedly secured to the anchor portion 54. The resilient nature of the closure enables the enlarged head portion 52 to conform to the surface 58 of the interior of the artery 24 contiguous with the puncture 28 so that its proximal surface 42 intimately engages the artery surface 58 while the hub-like anchor portion 54 extends somewhat into the puncture 28 to hemostatically seal the puncture when the closure is pulled into place, as will be described hereinafter.

Thus, as shown in FIG. 3, after the tubular body 32 of device 20 has been inserted into the sheath 26 so that its outlet 34 is within the artery, the sheath 26 is withdrawn. The pusher is then extended or pushed down the tubular body as described heretofore so that its distal end portion 40 forces the closure 30 out of outlet 34. Once the closure 30 is outside the confines of the tubular body 32 it expands or enlarges to its disk-shaped configuration. After the closure is pushed out of the tubular member by the pusher, the tubular body is itself withdrawn from the puncture 28 in the artery and moved completely outside the body of the patient. This action leaves the closure 30 within the artery and with the retraction filament extending through the puncture 28 so that a substantial portion of the filament is outside the patient's body. The filament is then pulled by its proximal end to cause the closure to move toward the puncture 28, until its anchor portion 42 is somewhat within the puncture and its engagement surface 50 is in intimate engagement with the interior of the artery wall contiguous with the puncture. This action hemostatically seals the puncture. In order to hold the closure in place the thread 34 is held taut and is secured in position on the patients skin, such as by use of a strip of conventional tape 60. Alternatively, some other gripping means (not shown) can be used to slide down the filament into contact with the skin while together gripping the filament tightly to prevent it from slipping.

By virtue of the fact that the head portion 52 of the closure is thin and conforms to the interior surface of the artery, it does not block off or otherwise impede the flow of blood through the artery.

It should be noted at this juncture that the closure can be of a suitable shape, and need not be of the disk-like shape shown herein, so long as once it is pulled into position at the situs of the puncture it serves to hemostatically seal that puncture without appreciably blocking the passageway.

As mentioned earlier the closure and its retraction filament are each preferably formed of an absorbable (e.g., biodegradable) material. This feature enables the closure to be left in place after hemostatis has occurred since it will be absorbed by the bodily tissues thereafter. Accordingly the closure does not have to be removed after having served its purpose.

In order to accelerate hemostasis the material forming the closure 30 may include conventional clotting agents, such as tissue thromboplastin. Moreover, in order to minimize the risks of thrombosis in the artery the front (distal) face 56 of the closure 30, which is exposed to the flow of blood through the artery, may be coated with a non-thrombogenic material. This feature serves to minimize the risk of thrombosis forming in the artery. The thrombogenic material used can comprise a waxy coating, such as coconut oil, on the closure's front surface 56.

Without further elaboration the foregoing will so fully illustrate my invention that others may, by applying current or future knowledge, adopt the same for use under various conditions of service.

What we claim is as follows:

1. A method for sealing a small incision or puncture in tissue separating one portion of the body of a living being from another portion thereof to prevent the flow of a bodily fluid from said one portion to said other portion through said incision or puncture by the introduction of plug means therein, said plug means being formed of a material which the body will absorb, said method comprising introducing said plug means into said incision or puncture, said plug means having a first portion extending into said incision or puncture and a second portion configured to conform to the surface of the tissue contiguous with said incision or puncture, and causing said plug means to engage said tissue so that said first portion intimately engages the tissue in said incision or puncture and the second portion intimately engages the surface of said tissue contiguous with said incision or puncture to seal said incision or puncture and thereby prevent communication between said body portions through said incision or puncture, and thereafter leaving said plug means in place, whereupon said incision or puncture is permanently sealed.

2. The method of claim 1 wherein said plug means hemostatically seals said opening.

3. The method of claim 1 wherein said plug means is in a compacted condition when introduced into said one portion of the body and is enabled to expand thereafter.

4. The method of claim 3 wherein said plug means when expanded does not appreciably block the interior of said other portion of the body.

5. The method of claim 1 wherein said method additionally comprises retracting said plug means to bring said plug means into engagement with said tissue after said plug means has been introduced into said one portion of the body.

6. The method of claim 5 additionally comprising holding said plug means in engagement with said tissue.

7. The method of claim 1 wherein said plug means is formed of a porous, hemostatic absorbable gelatin.

8. A device for sealing a small incision or puncture in tissue separating one portion of the body of a living being from another portion thereof to prevent the flow of a bodily fluid from said one portion to said other portion through said incision or puncture, comprising introducer means and plug means, said introducer means being adapted to be inserted into the body of said being for introducing said plug means into said incision or puncture, said plug means comprising a material which the body will absorb and having a first portion for extending into said incision or puncture and a second portion to conform to the surface of the tissue contiguous with said incision or puncture, whereupon when said introducer means introduces said plug means into said incision or puncture said first portion of said plug means intimately engages the tissue in said incision or puncture and said second portion intimately engages the surface of said tissue contiguous with said incision or puncture to seal said incision or puncture and thereby prevent communication between said body portions through said incision or puncture.

9. The device of claim 8 wherein said plug means is expandable and wherein said plug means is in a compact condition when introduced in said incision or puncture and thereafter expands.

10. The device of claim 9 wherein said plug means, when expanded, comprises an enlarged head portion of substantial area, but being substantially thin.

11. The device of claim 8 wherein said material comprises a porous, hemostatic absorbable gelatin.

12. A device for sealing a small incision or puncture in tissue separating one portion of the body of a living being from another portion thereof to prevent the flow of a bodily fluid from said one portion to said other portion through said incision or puncture, comprising introducer means and plug means, said introducer means being adapted to be inserted into the body of said being for introducing said plug means into said incision or puncture, said plug means comprising a first portion for extending into said incision or puncture, a second portion to conform to the surface of the tissue contiguous with said incision or puncture, and retraction means, said retraction means enabling said plug means to be drawn into engagement with said tissue after said plug means has been introduced into said incision or puncture, whereupon said first portion of said plug means intimately engages the tissue in said incision or puncture and said second portion intimately engages the surface of said tissue contiguous with said incision or puncture to seal said incision or puncture and thereby prevent communication between said body portions through said incision or puncture.

13. The device of claim 12 wherein said retraction means comprises a filament connected to said plug means.

14. A device for sealing a small incision or puncture in tissue separating one portion of the body of a living being from another portion thereof to prevent the flow of a bodily fluid from said one portion to said other portion through said incision or puncture, comprising introducer means and plug means, said introducer means being adapted to being inserted into the body of said being for introducing said plug means into said incision or puncture and comprising tubular means having an outlet adjacent the distal end thereof and ejector means, said tubular means to be inserted through said incision or puncture so that said outlet is located within one of said body portions, said ejector means being operative for causing said plug means to pass out of said outlet into said one body portion, said plug means comprising a first portion for extending into said incision or puncture and a second portion to conform to the surface of the tissue contiguous with said incision or puncture, whereupon when said introducer means introduces said plug means into said incision or puncture, said first portion of said plug means intimately engages the tissue in said incision or puncture and said second portion intimately engages the surface of said tissue contiguous with said incision or puncture to seal said incision or puncture and thereby prevent communication between said body portions through said incision or puncture.

15. The device of claim 14 wherein said ejector means comprises a pusher member located within said tubular means to force said plug means out of said outlet.

16. A device for sealing a small incision or puncture in tissue separating one portion of the body of a living being from another portion to prevent the flow of a bodily fluid from said one portion to said other portion through said incision or puncture, comprising plug means adapted to be inserted into the body of said being, said plug means comprising a material which the body will absorb and having a first portion for extending into said incision or puncture and a second portion to conform to the surface of the tissue contiguous with said incision or puncture, whereupon when said plug means is introduced into said incision or puncture, said first portion of said plug means intimately engages the tissue in said incision or puncture and said second portion intimately engages the surface of said tissue contiguous with said incision or puncture to seal said incision or puncture and thereby prevent communication between said portions through said incision or puncture.

17. The device of claim 16 wherein said plug means is expandable and wherein said plug means is in a compact condition when it is introduced into said incision or puncture and thereafter expands.

18. The device of claim 16 wherein said plug means additionally comprises retraction means to enable said plug means to be drawn into engagement with said tissue after said plug means has been introduced into said incision or puncture.

19. The device of claim 16 wherein said material comprises a porous, hemostatic absorbable gelatin.

* * * * *